United States Patent
Kourtakis et al.

(10) Patent No.: US 7,705,192 B2
(45) Date of Patent: Apr. 27, 2010

(54) CATALYTIC CONVERSION OF ETHANOL AND METHANOL TO AN ISOBUTANOL-CONTAINING REACTION PRODUCT USING A THERMALLY DECOMPOSED HYDROTALCITE CATALYST

(75) Inventors: Kostantinos Kourtakis, Media, PA (US); Michael B. D'Amore, Wilmington, DE (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 55 days.

(21) Appl. No.: 12/196,518

(22) Filed: Aug. 22, 2008

(65) Prior Publication Data

US 2009/0054706 A1 Feb. 26, 2009

Related U.S. Application Data

(60) Provisional application No. 60/965,701, filed on Aug. 22, 2007.

(51) Int. Cl.
*C07C 29/34* (2006.01)
*C07C 29/32* (2006.01)
(52) U.S. Cl. ............. 568/902.2; 568/902; 568/905
(58) Field of Classification Search ......... 568/902, 568/902.2, 905
See application file for complete search history.

(56) References Cited

U.S. PATENT DOCUMENTS 5,095,156 A 3/1992 Radlowski et al.
5,300,695 A 4/1994 Radlowski
5,559,275 A 9/1996 Barger

OTHER PUBLICATIONS

International Search Report and Written Opinion, PCT/US2008/074018, Aug. 22, 2008.
J. I. DiCosimo et al., Structure and Surface and Catalytic Properties of Mg-Al Basic Oxides.
J. Logsdon, Kirk-Othmer Encyclopedia of Chemical Technology, 2001, John Wiley & Sons, (Books Not Included).
J. I. DiCosimo et al., Structural Requirements and Reaction Pathways in Condensation Reactions of Alcohols on Mg AlO Catalysts, Journal of Catalysis, 2000, vol. 190:261-275.
C. Carlini et al., Guerbet Condensation of Methanol With N-Propanol to Isobutyl Alcohol Over Heterogenous Bifunctional Catalysts Based on Mg—Al Mixed Oxides Partially Sunstituted by Different Metal Components, Journal of Molecular Catalysis A: Chemical, 2005, vol. 232:13-20.
C. Carlini et al., Guerbet Condensation of Methanol With N-Propanol to Isobutyl Alcohol Over Heterogenous Copper Chromite/Mg—Al Mixed Oxides Catalysts, Journal of Molecular Catalysis A:Chemical, 2004, vol. 220:215-220.
V. K. Diez et al., Effect of the Acid-Base Properties of Mg—Al Mixed Oxides on the Catalyst Deactivation During Adol Condensation Reactions, Latin American Applied Research, 2003, vol. 33:79-86.
N. N. Das et al., Catalytic Characterization of Bi-Functional Catalysts Derived From Pd—Mg—Al Layered Double Hydroxides, Bull. Mater. Sci., 2002, vol. 25:283-289.
H. S. Fogler, Elements of Chemical Reaction Engineering, 2nd Edition, 1992 (Book Not Included).

*Primary Examiner*—Elvis O Price

(57) ABSTRACT

Hydrotalcites are partially or fully thermally decomposed to provide catalysts useful for the conversion of ethanol plus methanol to a reaction product comprising isobutanol.

11 Claims, 2 Drawing Sheets

CATALYTIC CONVERSION OF ETHANOL AND METHANOL TO AN ISOBUTANOL-CONTAINING REACTION PRODUCT USING A THERMALLY DECOMPOSED HYDROTALCITE CATALYST

CROSS-REFERENCE TO RELATED APPLICATIONS

This application claims benefit of priority from Provisional Application No. 60/965,701, filed Aug. 22, 2007. This application relates to commonly-assigned applications filed concurrently on Aug. 22, 2008.

FIELD OF THE INVENTION

The present invention relates to the catalytic conversion of ethanol plus methanol to an isobutanol-containing reaction product. Various organic chemicals, including isobutanol itself, can be separated from the reaction product. The catalysts are hydrotalcites, optionally containing transition metals, which have been thermally decomposed, either partially or fully, to form catalytically active species.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

Methods for producing isobutanol from methanol and other alcohols, particularly ethanol, are known. It is known that isobutanol can be prepared by condensation of ethanol and methanol over basic catalysts at high temperature using the so-called "Guerbet Reaction." See for example, J. Logsdon in Kirk-Othmer Encyclopedia of Chemical Technology, John Wiley and Sons, Inc., New York, 2001.

In addition, U.S. Pat. No. 5,300,695, assigned to Amoco Corp., discloses processes in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce an alcohol having X+Y carbons. In one specific embodiment, ethanol and methanol are used to produce isobutanol using a potassium L-type zeolite.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions.

Carlini et al. describe a catalytic reaction of methanol with n-propanol to produce isobutyl alcohol. The involved catalyst is a calcined hydrotalcite in combination with copper chromite. See C. Carlini et al, Journal of Molecular Catalysis A: Chemical (2005), 232 (1-2) 13-20. See also C. Carlini, Journal of Molecular Catalysis A: Chemical (2004), 220 (2), 215-220, in which the catalyst is a mixture of a hydrotalcite with palladium, nickel, rhodium or copper, with the mixture being calcined at 500° C.

Hydrotalcites are layered, double hydroxides of the general formula

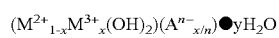
$$(M^{2+}_{1-x}M^{3+}_x(OH)_2)(A^{n-}_{x/n}) \bullet yH_2O$$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (*Latin American Applied Research*, 33, 79-86 (2003)) and N. N. Das and S. C. Srivastava (*Bull. Mater. Sci.* 25, (4), 283-289 (2002)).

It has been found that partially or fully thermally decomposed hydrotalcites, particularly those that incorporate transition metals, are catalysts that are effective for the conversion of ethanol plus methanol to a reaction product that comprises (i.e., contains, among other things) isobutanol.

SUMMARY OF THE INVENTION

Certain hydrotalcites, as described herein, are partially or fully thermally decomposed to provide catalysts useful for the conversion of ethanol plus methanol to an isobutanol-containing reaction product. Various organic chemicals, including isobutanol itself, or mixtures of organic chemicals, can be separated from the reaction product.

DESCRIPTION

Figure 1:
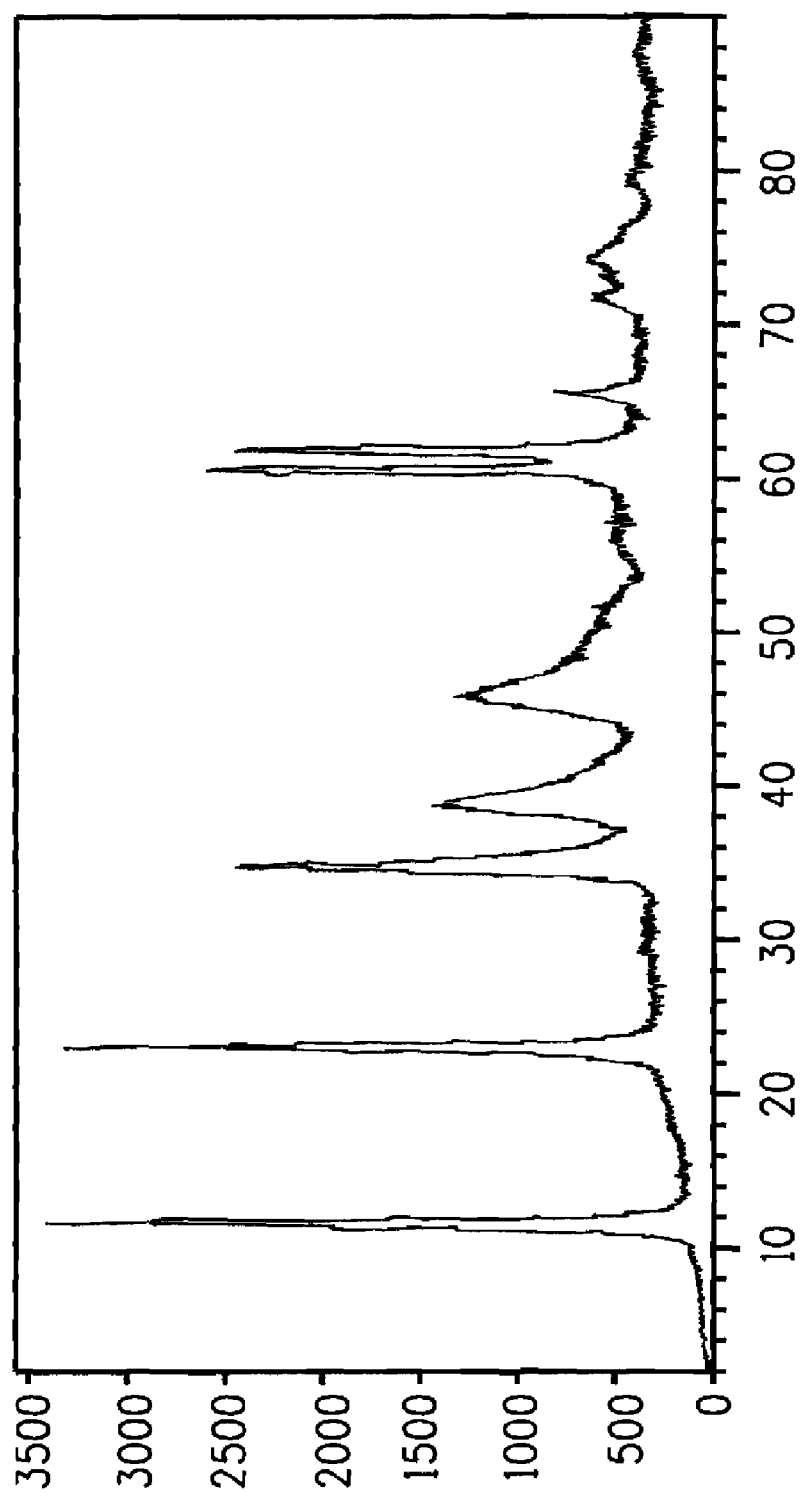
FIG. 1 shows the powder X-ray diffraction pattern of the hydrotalcite material of the Example before calcination, and indicates reflections typical of a hydrotalcite phase.
Figure 2:
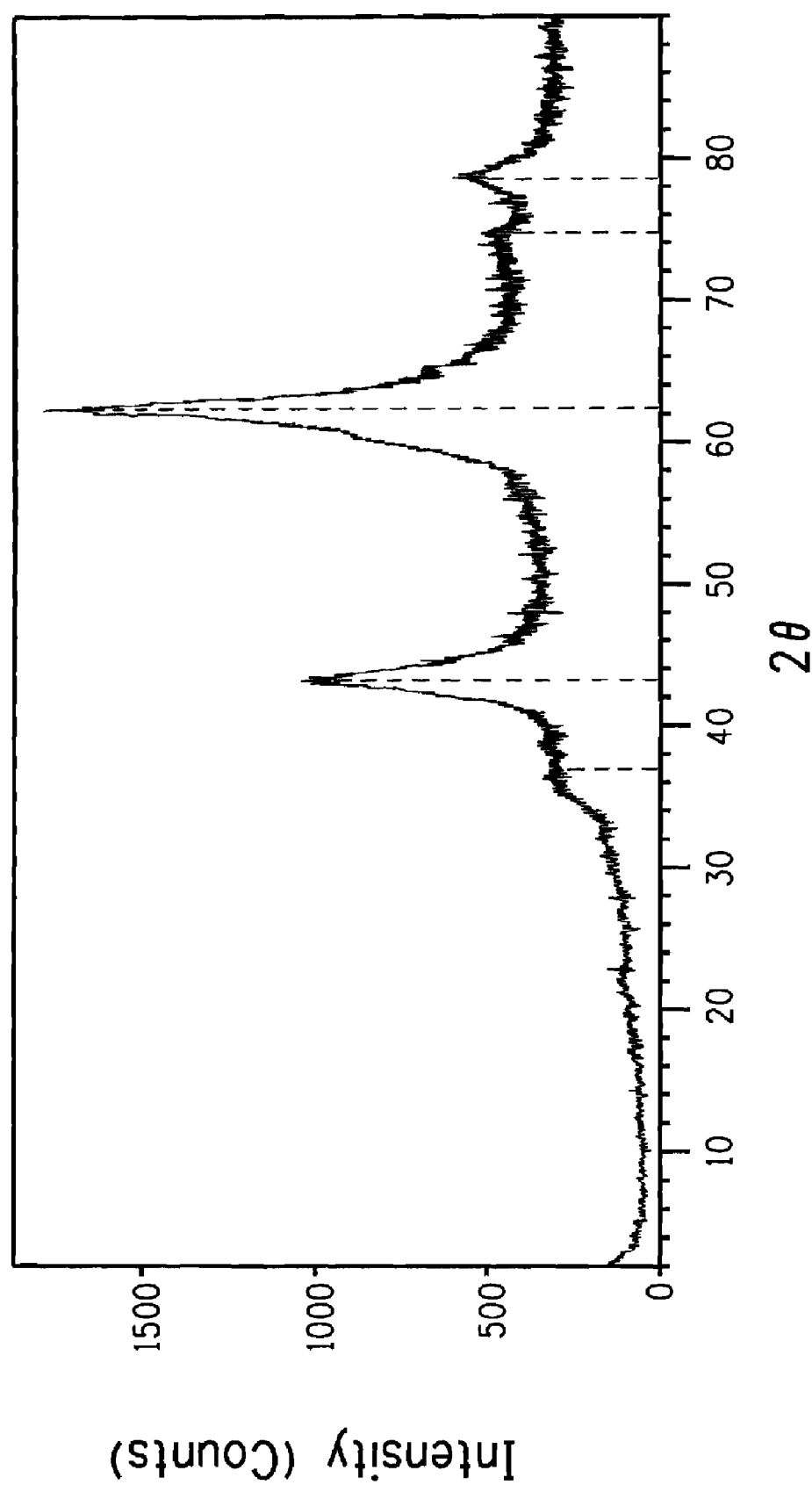
FIG. 2 shows the powder X-ray diffraction pattern of the material of FIG. 1 after calcination, showing decomposition of the hydrotalcite phase by the substantial loss of those reflections that are typical of a hydrotalcite phase.

A vapor stream comprising ethanol and methanol (that may contain some water, and may be diluted with an inert gas such as nitrogen and carbon dioxide) is contacted with at least one thermally decomposed hydrotalcite catalyst at a temperature and pressure sufficient to produce a reaction product comprising water, unreacted ethanol and/or methanol (if less than complete conversion of ethanol and/or methanol), and isobutanol. Butanols other than isobutanol, higher alcohols (higher in the sense that they contain more than 4 carbon atoms) and other organic species may also be produced. Suitable temperatures are in the range of about 150° C. to about 500° C., for example about 200° C. to about 500° C. Suitable pressures are from about 0.1 MPa to about 20.7 MPa. To optimize the production of isobutanol over other organic products, it is preferred that methanol and ethanol are used at a molar ratio of at least about 2 to 1.

The catalysts that are useful in the present invention are partially or fully thermally decomposed hydrotalcites of the empirical formula (prior to decomposition):

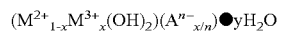
$$(M^{2+}_{1-x}M^{3+}_x(OH)_2)(A^{n-}_{x/n}) \bullet yH_2O$$

wherein $M^{2+}$ is divalent Mg, or a combination of divalent Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2, or $OH^-$ with n=1; and y is 0 to 4.

In a preferred embodiment, in the empirical formula, $M^{2+}$ is divalent Mg and at least one divalent member selected from the group consisting of Zn, Ni, Pd, Pt, Co, Fe, and Cu; $M^{3+}$ is trivalent Al; and $A^{n-}$ is $CO_3^{2-}$ (n=2) or $OH^-$ (n=1).

The catalysts that are useful in the present invention are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

Catalysts derived from the hydrotalcite can be synthesized by the following method. An aqueous salt solution containing (a) divalent magnesium, and, optionally, one or more divalent metals selected from the group consisting of zinc, nickel, palladium, platinum, cobalt, iron, and copper and (b) trivalent aluminum and, optionally, one or more trivalent metals selected from the group consisting of iron and chromium is prepared. Preferred salts are nitrates, chlorides, or acetates. Most preferred are nitrates. The salt solution is added to a basic, aqueous solution containing sodium or potassium carbonate (or bicarbonate), sodium, potassium or ammonium hydroxide, or a mixture of carbonate (or bicarbonate) and hydroxide. (Alternatively, a plurality of individual metal salt solutions may be used, provided that they are added concurrently to the basic, aqueous solution containing the carbonate, bicarbonate, hydroxide or mixtures thereof.) The pH of this basic solution is typically adjusted to a pH of approximately 10 during the addition of the aqueous salt solution. Preferably, the (a) magnesium and optional divalent metals and the (b) aluminum and optional trivalent metals are in a molar ratio (a)/(b) between 0.5/1 and 9/1 inclusive (i.e., including the endpoints 0.5/1 and 9/1 of the range).

The resulting suspension that is formed (i.e., a precipitate suspended in a liquid) can be aged, preferably for approximately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6 Al_2(CO_3)(OH)_{16}●4H_2O$ (JCPDS card # 54-1030; Powder Diffraction Files, International Centre for Diffraction Data, 1601 Park Lane, Swarthmore, Pa. 19081). The dried precipitate is then calcined, to achieve partial decomposition, by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card # 65-0476). Partial decomposition is preferably achieved by calcining the dried precipitate for a time and at a temperature sufficient to substantially reduce the peak intensities characteristic of the hydrotalcite phase.

Although any calcination protocol can be used, one that is particularly useful on a laboratory scale includes heating the hydrotalcite in a one inch (2.5 cm) diameter tube furnace from about 25° C. to about 360° C. over 140 minutes at 2.4° C. per minute, and then holding at 360° C. for about 2 to about 4 hours.

The catalysts usable in the process of the invention can be prepared as described above. The catalysts may be used in the form of powders, granules, or other particulate forms. Selection of an optimal average particle size for the catalyst will depend upon such process parameters as reactor residence time and desired reactor flow rates.

The catalytic conversion of ethanol plus methanol to the reaction product can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

It is preferable, but not essential, to treat the catalyst, prior to its use, with nitrogen or air at elevated temperatures, which is thought to remove unwanted carbonates from the catalyst surface. If the starting hydrotalcite contains nickel, palladium, platinum, cobalt or copper, it is also preferred, but not essential, to treat the catalyst, prior to its use, with hydrogen at elevated temperatures. One protocol that has been found to be effective is described in more detail in the Example, below. If catalyst treatment is desired, the catalyst may be treated in situ in the reactor or ex situ and then introduced into the reactor.

During the course of the reaction, the catalyst may become fouled, and, therefore, it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of isobutanol from the reaction.

Isobutanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of conversion of ethanol and methanol.

Although particular embodiments of the present invention have been described in the foregoing description, it will be understood by those skilled in the art that the invention is capable of numerous modifications, substitutions, and rearrangements without departing from the spirit or essential attributes of the invention.

EXAMPLES

Example 1

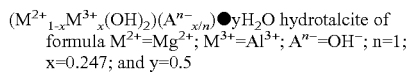
$(M^{2+}_{1-x}M^{3+}_x(OH)_2)(A^{n-}_{x/n})●yH_2O$ hydrotalcite of formula $M^{2+}=Mg^{2+}$; $M^{3+}=Al^{3+}$; $A^{n-}=OH^-$; n=1; x=0.247; and y=0.5

125 Milliliters (ml) of water was added to a three neck, round bottom flask and heated to 65° C. The pH was adjusted to about 10 by adding 2M NaOH solution (Mallinckrodt Baker, Phillipsburg, N.J.). 13.8 g of aluminum nitrate (Al$(NO_3)_3●9H_2O$ (EMD Sciences, Gibbstown, N.J.)) was dissolved in 50 ml of water, and 28.8 g of magnesium nitrate $(Mg(NO_3)_2●6H_2O$ (Sigma-Aldrich, St. Louis, Mo.)) was dissolved in 50 ml of water. These latter two solutions were added concurrently and drop-wise to the preheated NaOH solution. After complete addition of the metal nitrate solutions, the resulting suspension was kept at 65° C. with stirring for 1 hour and then aged at this temperature for 18 hours without stirring.

The precipitate was separated from solution by filtering and washed, twice, with about 250 ml of deionized water. The synthesized, separated solids were dried in vacuum oven at 90° C. for 24 hours and calcined at 360° C. for 2 hours in nitrogen. The heating protocol was as follows: The precipitate was placed in a 1 inch (2.5 cm) diameter tube furnace, and the temperature was increased from 25° C. to 360° C. at 2.4° C. per minute over the course of 140 minutes, followed by 360° C. for 2 hours.

Reactor Evaluation

Approximately 2 cubic centimeters (cc) of catalyst was loaded on a stainless steel mesh support within an 18"×½" (45.7 cm×1.3 cm) outside diameter (o.d.) type 360 stainless steel tube reactor with inlets for gas and liquid feeds. The catalyst was pre-conditioned in situ by flowing nitrogen gas through it at a flow rate of 15 cc/min, initially at room temperature, after which the reactor temperature was raised to 350° C., held there for one hour, and then lowered to 300° C. While maintaining the nitrogen flow, a mixed stream of methanol and ethanol at a weight ratio of 5 to 1 was introduced at a flow rate of 1.03 ml/hr to obtain reaction data at 300° C. (The reactor temperature was subsequently raised to 350 and then 400° C. to obtain reaction data at these two higher temperatures.) (If the catalyst had contained nickel, palladium, platinum, cobalt or copper, the pre-conditioning would have involved flowing nitrogen gas, initially at room temperature, raising the temperature to 350° C., holding it there for one hour, lowering the temperature to 180° C., flowing hydrogen gas at 15 cc/min for one hour, reintroducing nitrogen gas at a flow rate of 15 cc/min, and increasing the reactor temperature to 300° C. to introduce the mixed stream of ethanol and methanol to generate reaction data.) After 60 minutes, reaction off-gases were condensed over a five minute period into cold N-methylpyrrolidone, and the resulting solution was analyzed using an Agilent™ 5890 GC (Palo Alto, Calif.) equipped with flame ionization and mass selective detectors. Results are shown in the Table below, wherein "EtOH" means ethanol, "i-BuOH" means isobutanol, "Conv." means conversion, and "Sel." means selectivity. Ethanol conversion (%) was calculated as follows: [(1−carbon moles of unreacted ethanol)/carbon moles of total outlet gases] times 100. Selectivity (%) was calculated as follows: (moles of i-BuOH/moles of ethanol reacted) times 100.

TABLE 1

| Temp. ° C. | Minutes | EtOH Conv. | i-BuOH Sel. |
|---|---|---|---|
| 300 | 60 | 47.6 | 3.9 |
| 350 | 60 | 78.3 | 7.6 |
| 400 | 60 | 81.1 | 8.8 |

What is claimed is:

1. A process for making an isobutanol-containing product, said process comprising:
   contacting a reactant comprising ethanol and methanol with a catalyst at a reaction temperature and pressure sufficient to produce said product, wherein said catalyst is derived from a hydrotalcite of the formula:

$(M^{2+}_{1-x}M^{3+}_x(OH)_2)(A^{n-}_{x/n}) \bullet yH_2O$ wherein $M^{2+}$ is divalent Mg, or a combination of divalent Mg and at least one divalent member selected from the group consisting of Zn, Ni, Pd, Pt, Co, Fe, and Cu;
   $M^{3+}$ is trivalent Al, or a combination of trivalent Al and at least one trivalent member selected from the group consisting of Fe and Cr;
   x is 0.66 to 0.1;
   $A^{n-}$ is $CO_3^{2-}$ with n=2 or $OH^-$ with n=1; and
   y is 0 to 4;
   wherein the hydrotalcite catalyst is partially decomposed.

2. The process of claim 1, wherein the decomposition is achieved by heating for a time and at a temperature sufficient to cause a diminution in the hydrotalcite powder X-ray diffraction pattern peak intensities between 2θ angles of 10 degrees and 70 degrees using CuKα radiation.

3. The process of claim 1, wherein $M^{2+}$ is divalent Mg.

4. The process of claim 1, wherein $M^{3+}$ is trivalent Al.

5. The process of claim 1, wherein $A^{n-}$ is $OH^-$.

6. The process of claim 1, wherein n is 1.

7. The process of claim 1, wherein x is 0.247.

8. The process of claim 1, wherein y is 0.5.

9. The process of claim 1, wherein $M^{2+}$ is $Mg^{2+}$; $M^{3+}$ is $Al^{3+}$; $A^{n-}$ is $OH^-$; n is 1; x is 0.247; and y is 0.5.

10. The process of claim 1, wherein said reaction temperature is from about 200° C. to about 500° C., and said pressure is from about 0.1 MPa to about 20.7 MPa.

11. The process for making the isobutanol-containing product of claim 1, said process comprising:
    contacting a reactant comprising ethanol and methanol with a catalyst at a reaction temperature and pressure sufficient to produce said product, wherein said catalyst is made by a method comprising:
    a) dissolving a soluble (i) sodium or potassium carbonate or sodium or potassium bicarbonate, or (ii) sodium, potassium or ammonium hydroxide, or (iii) a mixture of (i) and (ii), in water to form a first solution and heating the first solution to between 60° C. and 70° C.;
    b) adjusting the pH of the first solution with hydroxide to a pH of approximately 10;
    c) adding to the first solution (i) at least one magnesium salt and optionally salts of one or more divalent metals selected from the group consisting of Zn, Ni, Pd, Pt, Co, Fe, and Cu; and (ii) at least one aluminum salt and optionally salts of one or more trivalent metals selected from the group consisting of Fe and Cr, wherein (a) said salts are in one or more aqueous solutions, and (b) the magnesium and optional divalent metals of (i) and the aluminum and optional trivalent metals of (ii) are in a molar ratio between 0.5/1 and 9/1 inclusive, thereby forming a suspension whose pH is maintained at approximately 10;
    d) optionally stirring the suspension and maintaining the suspension at a temperature between 60° C. and 70° C.;
    e) aging the suspension of step (c) or step (d) to form a precipitate and separating the precipitate from the suspension; and
    partially decomposing the precipitate by heating it for a time and at a temperature sufficient to cause a diminution in hydrotalcite powder X-ray diffraction pattern peak intensities between 2θ angles of 10 degrees and 70 degrees using CuKα radiation, thereby forming said catalyst.

* * * * *